(12) United States Patent
Cook et al.

(10) Patent No.: US 7,959,691 B2
(45) Date of Patent: *Jun. 14, 2011

(54) COMPOSITION

(75) Inventors: Stephen Leonard Cook, Chester (GB); Werner Kalischewski, Dorsten (DE); Gabriele Lohmann, Halteun (DE)

(73) Assignee: Innospec Deutschland GmbH, Herne (DE)

( * ) Notice: Subject to any disclaimer, the term of this patent is extended or adjusted under 35 U.S.C. 154(b) by 13 days.

This patent is subject to a terminal disclaimer.

(21) Appl. No.: 12/482,789

(22) Filed: Jun. 11, 2009

(65) Prior Publication Data
US 2009/0241412 A1 Oct. 1, 2009

(51) Int. Cl.
*C10L 1/30* (2006.01)

(52) U.S. Cl. ......................................................... 44/361

(58) Field of Classification Search .................... 44/361
See application file for complete search history.

(56) References Cited

U.S. PATENT DOCUMENTS

| 3,341,495 | A | * | 9/1967 | Neuse | 528/9 |
| 3,392,171 | A | | 7/1968 | Fonken | |
| 3,437,634 | A | * | 4/1969 | Neuse | 528/9 |
| 3,673,232 | A | | 6/1972 | Talbot et al. | |
| 3,989,731 | A | | 11/1976 | Talbot | |
| 4,389,220 | A | * | 6/1983 | Kracklauer | 44/361 |
| 4,946,609 | A | | 8/1990 | Pruess et al. | |
| 4,998,876 | A | * | 3/1991 | Farrar | 431/3 |
| 5,235,936 | A | | 8/1993 | Kracklauer | |
| 5,386,804 | A | | 2/1995 | Guttmann et al. | |
| 6,113,660 | A | * | 9/2000 | Hubbard et al. | 44/300 |
| 7,556,657 | B2 | * | 7/2009 | Cook et al. | 44/361 |

FOREIGN PATENT DOCUMENTS

| DE | 100 43 144 C1 | 12/2001 |
| DE | 201 10 995 U1 | 1/2002 |
| WO | WO 02/18398 A1 | 3/2002 |

* cited by examiner

*Primary Examiner* — Glenn Caldarola
*Assistant Examiner* — Jim Goloboy
(74) *Attorney, Agent, or Firm* — Fay Sharpe LLP

(57) ABSTRACT

The present invention provides a composition comprising: i) at least one compound of formula (I):

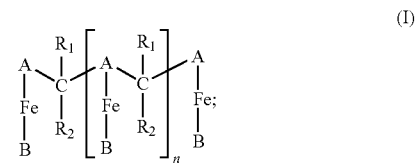

(I)

wherein $R_1$ and $R_2$ are independently selected from a group consisting of hydrogen, unsubstituted or substituted $C_{1-19}$ hydrocarbyl or a group of formula (II):

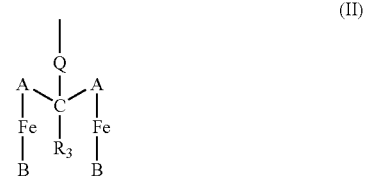

(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10; and ii) a diluent or carrier; wherein the compound(s) of formula (I) is present in an amount sufficient to provide, at −30° C., at least 1 wt % of iron, based on the weight of the composition.

39 Claims, No Drawings

COMPOSITION

This application claims the priority benefit of U.S. application Ser. No. 10/488,134, filed Aug. 12, 2004, the disclosure of which is incorporated herein by reference.

The present invention relates to a composition. In particular the present invention relates to a composition which may be used in the regeneration of particulate filter systems which receive exhaust gases from a combustion system.

Diesel particulate emissions are perceived as a health problem. One solution to this problem is to filter the carbonaceous material from exhaust gas. Devices capable of doing this are well known. Such filters must be periodically regenerated by combustion of the carbonaceous deposits. The effect which iron-organic compounds, particularly ferrocene and derivatives thereof, have in promoting combustion is known both with respect to open flame combustion as well as combustion in engines. Furthermore, the prior art (e.g. Fuels 1999, $2^{nd}$ International Colloquium, 20-21 Jan. 1999 at Esslingen Technical Academy) discloses that diesel particulate filters (DPFs) can be regenerated by additives in diesel fuel since the products of combustion to which the additive gives rise reduce the ignition temperature of the soot particles which have been filtered out in the diesel particulate filter (DPF), these latter particles igniting and burning away.

Since iron-organic compounds, such as ferrocene, in solid form are not ideal for dosing to the fuel, dosing may be conveniently carried out using readily diesel-soluble and fully diesel-compatible solutions of the compounds or one or more iron-organic compound(s) that are liquid at the temperature of use. It is desirable, particularly when the combustion system is located on a vehicle, for any solutions containing the iron-organic compounds to be highly concentrated solutions so that the additive supply container can be as small as possible in size, or, rather, does not need to be frequently topped up.

Ferrocene itself has a solubility limit of 2.4% by weight at $-40°$ C. corresponding to an iron content of 0.72% by weight in a highly aromatic solvent (PLUTOsol™ APF, supplied by Octel Deutschland GmbH). In a non-aromatic solvent (Isopar L) ferrocene provides an iron content of only 0.22% by weight at $-30°$ C. Solutions of iron-organic compounds with an iron content of more than 1.0% by weight, preferably more than 2.5% by weight and more preferably more than 4.0% by weight at $-40°$ C. are sought. Preferred solvents are low-aromatic or non-aromatic solvents including the Isopar™ range as this allows a wider selection of materials, in particular polymers, especially HDPE, to be used in the construction of the additive supply container and pumping/delivery system.

HDPE is a low-cost widely-used material, which is not normally compatible with highly aromatic solvents. Where aromatic solvents are used in HDPE additive supply containers, distortion or swelling of the containers may occur, such that physical changes and degradation can be expected. These aspects are not compatible with the necessary 12-15 year life of the container. Furthermore, aromatic solvents may permeate the walls of an HDPE container, such that solvent is lost over time resulting in increased solution viscosity and undesirable changes in the characteristics of the additive formulation.

Concentration effects due to solvent loss may lead to an increase in iron-organic compound content, thus altering the active content of iron treated to the fuel. This may affect the regeneration process and may lead to excessive exothermic heat of reaction inside the DPF during regeneration. Ceramic DPF materials may be adversely affected, resulting in cracking or other damage from thermal shock. Furthermore, ash accumulation, which is a natural process eventually requiring the washing out of the filter, may accelerate where an excessive iron treat rate results from solvent loss induced concentration effects.

HDPE containers can be modified to increase their compatibility with aromatic solvents. The process involves forming a barrier or lining inside the container in order to prevent swelling and distortion of the container and loss of solvent by permeation through the walls. A suitable barrier or lining can be provided by a process called co-extrusion, where containers are fabricated by blow-moulding. Where containers are made by injection moulding, a barrier can be created by post-manufacture fluorination. Co-extrusion with a polyamide layer, or fluorination to level 5 after injection moulding are techniques well known to those skilled in the art.

There are significant disadvantages to the prior art methods of adapting HDPE containers to allow the storage of additives formulated with aromatic solvents. The need to provide a barrier to prevent solvent loss by permeation, and also to prevent swelling and distortion which would otherwise occur when storing aromatic solvents in HDPE containers imposes a significant cost penalty on the storage of an additive formulated with an aromatic solvent. Similarly, there is a penalty in manufacturing logistics incurred by the need to fluorinate containers after injection moulding, or alternatively a lack of flexibility incurred by the need to co-extrude a barrier liner with HDPE in a blow moulding process. A further disadvantage of HDPE containers which have been adapted to increase compatibility with aromatic solvent is that they are more difficult to recycle than containers consisting solely of or consisting mainly of HDPE. It is becoming increasingly important for vehicle components to be easily recycled as in the future vehicles will be recycled at the end of their useful life-time. It is therefore greatly preferred to formulate an additive with a low-aromatic or non-aromatic solvent to reduce costs, eliminate manufacturing logistics problems and avoid recycling problems.

The present invention alleviates the problems of the prior art.

In one aspect the present invention provides a composition comprising: i) at least one compound of formula (I):

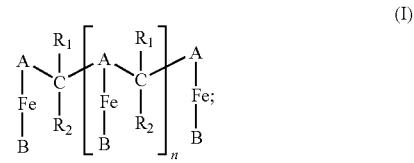

wherein $R_1$ and $R_2$ are independently selected from a group consisting of hydrogen, unsubstituted or substituted $C_{1-19}$ hydrocarbyl or a group of formula (II):

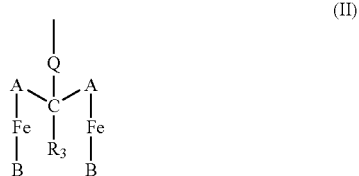

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10; and ii) a diluent or carrier; wherein the compound(s) of formula (I) is present in an amount sufficient to provide, at −30° C., at least 1 wt % of iron, based on the weight of the composition.

In one aspect the present invention provides a fuel additive dosing apparatus comprising a supply container formed from a plastics material incompatible with an aromatic diluent or carrier and a composition contained within the supply container comprising: i) at least one compound of formula (I):

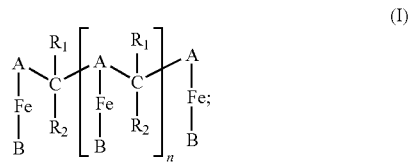

(I)

wherein $R_1$ and $R_2$ are independently selected from a group consisting of hydrogen, unsubstituted or substituted $C_{1-19}$ hydrocarbyl or a group of formula (II):

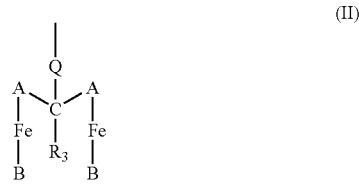

(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10; and ii) a low aromatic or non-aromatic diluent or carrier.

In one aspect the present invention provides a fuel composition comprising (a) a fuel; and (b) a compound of formula (I):

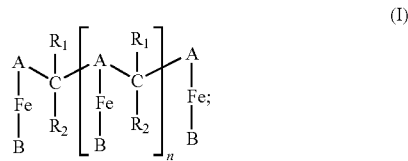

(I)

wherein $R_1$ and $R_2$ are independently selected from a group consisting of hydrogen, unsubstituted or substituted $C_{1-19}$ hydrocarbyl or a group of formula (II):

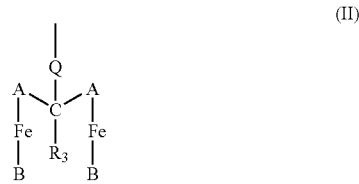

(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10.

In one aspect the present invention provides a method of regenerating a particulate filter located in an exhaust system of a combustion system for fuel, which comprises contacting carbon-based particulates, present in the particulate filter, with combustion products of a composition as herein defined.

In one aspect the present invention provides use of a composition as herein defined for decreasing the regeneration temperature of a particulate filter located in the exhaust system of a combustion system.

It has been found that compounds of the present invention advantageously have a high degree of solubility or dispersibility, preferably solubility, in the diluent or carrier present in the composition according to the present invention. Additionally, the composition of the invention advantageously has temperature stability across a wide temperature range. In particular, no stability problems should result within the range of from −30° C. to +90° C., and preferably within the range of from −40° C. to +90° C. It has surprisingly been shown that the composition of the present invention may provide a composition having an iron content of up to 10 wt %, which is stable down to −30° C., and partially stable down to −40° C. and beyond. Further, it has been found that such solutions containing 2.5 wt % iron are stable at −40° C.

A further advantage of the present invention is the provision of compositions the viscosity of which is not too greatly increased within the low temperature range. This could otherwise have adverse effects upon the pumpability of the composition and could, for example, result in difficulties in conjunction with a metering pump. In this connection, the viscosity of the composition according to the present invention, having an iron content of 2.5% by weight, is advantageously less than, or approximately equal to, 25 mPas at a temperature of −40° C.

The term "hydrocarbyl" as used herein relates to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, silicon and phosphorus. Of these heteroatoms oxygen is particularly preferred. Therefore, in one aspect the hydrocarbyl group may for example be an alkoxy group.

Each hydrocarbyl group including the unsaturated cyclic hydrocarbyl group of A and the unsaturated cyclic hydrocarbyl group of B may optionally be substituted with one or more substituent. Any such substituent is preferably inert under the reaction conditions employed in the preparation of the compounds of formula (I) and preferably should not give unfavourable interactions with a liquid hydrocarbon fuel or other additives employed in such a fuel. Substituents meeting these conditions will be readily apparent to a person skilled in the art.

Examples of suitable substituents are alkyl, substituted alkyl, alkoxy, substituted alkoxy, aryl, substituted aryl, arylalkyl, substituted arylalkyl groups and cyclic groups such as cycloalkyl. In addition to the possibility of the substituents being a cyclic group, a combination of substituents may form a cyclic group. Suitable substituents for the substituted groups include alkyl, halo, hydroxy, nitro, alkoxy, aryl, cyclic, ester groups and combinations thereof. In the case of substituted arylalkyl groups, the substituent or substituents may be present on the aryl and/or the alkyl portion of the group. The term "alkyl" or the alkyl portion of an alkoxy or arylalkyl group, may be straight chain or branched chain.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

A typical hydrocarbon group is an alkyl group.

The hydrocarbyl/hydrocarbon/alkyl may be straight chain or branched and/or may be saturated or unsaturated.

By the term "$R_1$—C—$R_2$ backbone" it is meant the longest chain of directly bonded atoms within the $R_1$—C—$R_2$ moiety. It will be understood that a chain does not include atoms of cyclic substituents or substituents of a terminal carbon.

Unless otherwise stated the weight percent (wt %) of iron is measured at –30° C. and 1 atmosphere pressure.

By the term "plastics material incompatible with aromatic diluent or carrier" it is meant a plastics material which undergoes distortion and/or which exhibits mean solvent loss of an aromatic diluent or carrier by permeation of greater than 2% per year, such as greater than 5%, or such as greater than 10% per year.

The term "aromatic" as used herein relates to a diluent or carrier with a total aromatic substance content of greater than 98% by weight. Typical aromatic substances are aromatic compounds having 9 to 16 carbon atoms and a boiling range of 170° C. to 295° C. PLUTOsol™ APF is an example of an aromatic diluent or carrier.

The term "non-aromatic or low-aromatic" as used herein relates to a diluent or carrier with a total aromatic substance content of less than 30 wt %. Preferably, the term "non-aromatic or low-aromatic" as used herein relates to a diluent or carrier with a total aromatic substance content of less than 20 wt %, preferably less than 10 wt %, preferably less than 5 wt %, preferably less than 1 wt % such as less than 0.5 wt %, preferably less than 0.1 wt % such as less than 0.05 wt %. Isopar L is an example of a non-aromatic or low-aromatic diluent or carrier and has a total aromatic substance content of less than 0.05 wt %.

The term "carbon-based particulates", as used herein, includes carbon-based particulates which are typically formed by incomplete combustion of the fuel within the combustion system but which may also be formed from combustion of lubricating oil or other organic-based materials used within the combustion system. Typical carbon-based particles include soot particles.

The term "regeneration temperature" as used herein relates to the minimum exhaust gas temperature at which trapped carbon-based particulates may be oxidised to gaseous products. The regeneration temperature may also be defined as the exhaust gas temperature at which the rate of deposit of carbon-based particulates on the diesel particle filter is equal to the rate of removal of carbon-based particulates from the diesel particle filter by oxidation to gaseous products. This is known as the balance point of the DPF. Further details on balance points and methods of determining them may be found in U.S. Pat. No. 6,003,303 or in P L Herzog, 2000, ATA, vol. 53, No. 11/12, pages 389-397.

Composition

As previously mentioned, in one aspect the present invention provides a composition comprising: i) at least one compound of formula (I):

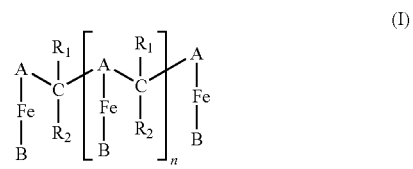

wherein $R_1$ and $R_2$ are independently selected from a group consisting of hydrogen, unsubstituted or substituted $C_{1-19}$ hydrocarbyl or a group of formula (II):

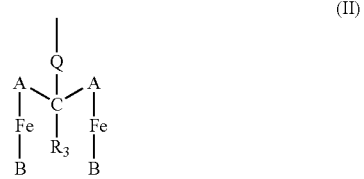

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10; and ii) a diluent or carrier; wherein the compound(s) of formula (I) is present in an amount sufficient to provide, at –30° C., at least 1 wt % of iron, based on the weight of the composition.

Diluent or Carrier

In one aspect the diluent or carrier is a solvent. In one aspect the diluent or carrier is a low-aromatic or non-aromatic diluent or carrier. In one aspect the diluent or carrier is a low-aromatic or non-aromatic solvent.

It will be readily understood that the compound(s) of formula (I) may be dissolved in the diluent or carrier to form a solution or may be suspended in the diluent or carrier to form a suspension. In one aspect a proportion of the compound(s) of formula (I) is dissolved in the diluent or carrier and a proportion of the compound(s) of formula (I) is suspended in the diluent or carrier. In a preferred aspect substantially all of the compound(s) of formula (I) is dissolved in the diluent or carrier. By the term "substantially all" is meant more than 90%, preferably more than 95%, preferably more than 98% of the compound(s) of formula (I).

Preferred diluents or carriers are low-aromatic or non-aromatic diluents or carriers which have an initial boiling point of greater than 100° C., preferably at least 160° C. and consequently have low vapour pressure, such that evaporative loss does not lead to significant changes in iron concentration on long-term storage. Preferred non-aromatic or low-aromatic diluents or carriers are those with a total aromatic substance content of less than 10% by weight, preferably less than 1% by weight, preferably less than 0.5% by weight. An example of a preferred non-aromatic or low-aromatic diluent or carrier is Isopar L.

The use of a non-aromatic or low-aromatic diluent or carrier improves ease of handling and storage in particular with regard to health and safety considerations and also allows compatibility with supply containers formed from a range of plastics materials such as HDPE.

$R_1$—C—$R_2$

In one aspect when the $R_1$—C—$R_2$ backbone is 5, 7 or 19 atoms in length, the backbone is substituted.

In one aspect the $R_1$—C—$R_2$ backbone is substituted.

In one aspect the $R_1$—C—$R_2$ backbone is from 6 to 20 atoms in length. In one aspect the $R_1$—C—$R_2$ backbone is from 7 to 20 atoms in length. In one aspect the $R_1$—C—$R_2$ backbone is from 8 to 20 atoms in length. In one aspect, the $R_1$—C—$R_2$ backbone is from 14 to 20 atoms in length.

In one aspect the $R_1$—C—$R_2$ backbone is from 5 to 18 atoms in length, preferably 6 to 18 atoms in length, preferably 8 to 18 atoms in length, preferably 14 to 18 atoms in length.

In one preferred aspect the $R_1$—C—$R_2$ backbone is from 7 to 10 atoms in length. In one aspect the $R_1$—C—$R_2$ backbone is 7 atoms in length. In one aspect the $R_1$—C—$R_2$ backbone is 8 atoms in length. In one aspect the $R_1$—C—$R_2$ backbone is 9 atoms in length. In one aspect the $R_1$—C—$R_2$ backbone is 10 atoms in length.

$R_1$ and $R_2$

In one aspect $R_1$ and $R_2$ are independently selected from H and unsubstituted or substituted $C_{1-19}$ hydrocarbyl group. In one aspect $R_1$ and $R_2$ are independently selected from H and unsubstituted or substituted $C_{4-19}$ hydrocarbyl group. In one aspect $R_1$ and $R_2$ are independently selected from H and unsubstituted or substituted $C_{4-10}$ hydrocarbyl group. In one aspect $R_1$ and $R_2$ are independently selected from H and unsubstituted or substituted $C_{7-19}$ hydrocarbyl group. In one aspect $R_1$ and $R_2$ are independently selected from H and unsubstituted or substituted $C_{7-10}$ hydrocarbyl group.

In one aspect $R_1$ and $R_2$ are independently selected from H and unsubstituted or substituted $C_{1-19}$ hydrocarbon group. In one aspect $R_1$ and $R_2$ are independently selected from H and unsubstituted or substituted $C_{4-19}$ hydrocarbon group. In one aspect $R_1$ and $R_2$ are independently selected from H and unsubstituted or substituted $C_{4-10}$ hydrocarbon group. In one aspect $R_1$ and $R_2$ are independently selected from H and unsubstituted or substituted $C_{7-19}$ hydrocarbon group. In one aspect $R_1$ and $R_2$ are independently selected from H and unsubstituted or substituted $C_{7-10}$ hydrocarbon group.

The term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In one aspect $R_1$ and $R_2$ are independently selected from H and unsubstituted or substituted $C_{1-19}$ alkyl group. In one aspect $R_1$ and $R_2$ are independently selected from H and unsubstituted or substituted $C_{4-19}$ alkyl group. In one aspect $R_1$ and $R_2$ are independently selected from H and unsubstituted or substituted $C_{4-10}$ alkyl group. In one aspect $R_1$ and $R_2$ are independently selected from H and unsubstituted or substituted $C_{7-19}$ alkyl group. In one aspect $R_1$ and $R_2$ are independently selected from H and unsubstituted or substituted $C_{7-10}$ alkyl group.

In one aspect at least one $R_1$ group is independently selected from hydrogen, methyl and ethyl. In a preferred aspect each $R_1$ group is independently selected from hydrogen, methyl and ethyl.

In one aspect at least one $R_1$ group is hydrogen. In a preferred aspect each $R_1$ group is hydrogen.

In one aspect at least one $R_1$ group is methyl. In a preferred aspect each $R_1$ group is methyl.

In one aspect at least one $R_1$ group is ethyl. In a preferred aspect each $R_1$ group is ethyl.

In one aspect at least one $R_2$ group is a group selected from an unsubstituted or substituted $C_{2-19}$ hydrocarbyl group, an unsubstituted or substituted $C_{3-19}$ hydrocarbyl group, an unsubstituted or substituted $C_{4-9}$ hydrocarbyl group, an unsubstituted or substituted $C_{5-19}$ hydrocarbyl group, an unsubstituted or substituted $C_{6-19}$ hydrocarbyl group, an unsubstituted or substituted $C_{7-19}$ hydrocarbyl group, an unsubstituted or substituted $C_{6-15}$ hydrocarbyl group, an unsubstituted or substituted $C_{7-15}$ hydrocarbyl group, an unsubstituted or substituted $C_{4-10}$ hydrocarbyl group, an unsubstituted or substituted $C_{6-10}$ hydrocarbyl group, and an unsubstituted or substituted $C_{7-10}$ hydrocarbyl group.

In one aspect at least one $R_2$ group is a group selected from an unsubstituted or substituted $C_{2-19}$ hydrocarbon group, an unsubstituted or substituted $C_{3-19}$ hydrocarbon group, an unsubstituted or substituted $C_{4-19}$ hydrocarbon group, an unsubstituted or substituted $C_{5-19}$ hydrocarbon group, an unsubstituted or substituted $C_{6-19}$ hydrocarbon group, an unsubstituted or substituted $C_{7-19}$ hydrocarbon group, an unsubstituted or substituted $C_{6-15}$ hydrocarbon group, an unsubstituted or substituted $C_{7-15}$ hydrocarbon group, an unsubstituted or substituted $C_{4-10}$ hydrocarbon group, an unsubstituted or substituted $C_{6-10}$ hydrocarbon group, and an unsubstituted or substituted $C_{7-10}$ hydrocarbon group.

In one aspect at least one $R_2$ group is a group selected from an unsubstituted or substituted $C_{2-19}$ alkyl group, an unsubstituted or substituted $C_{3-19}$ alkyl group, an unsubstituted or substituted $C_{4-19}$ alkyl group, an unsubstituted or substituted $C_{5-19}$ alkyl group, an unsubstituted or substituted $C_{6-19}$ alkyl group, an unsubstituted or substituted $C_{7-19}$ alkyl group, an unsubstituted or substituted $C_{6-15}$ alkyl group, an unsubstituted or substituted $C_{7-15}$ alkyl group, an unsubstituted or substituted $C_{4-10}$ alkyl group, an unsubstituted or substituted $C_{6-10}$ alkyl group, and an unsubstituted or substituted $C_{7-10}$ alkyl group.

In one aspect each $R_2$ group is a group selected from an unsubstituted or substituted $C_{2-19}$ hydrocarbyl group, an unsubstituted or substituted $C_{3-19}$ hydrocarbyl group, an unsubstituted or substituted $C_{4-19}$ hydrocarbyl group, an unsubstituted or substituted $C_{5-19}$ hydrocarbyl group, an unsubstituted or substituted $C_{6-19}$ hydrocarbyl group, an unsubstituted or substituted $C_{7-19}$ hydrocarbyl group, an unsubstituted or substituted $C_{6-15}$ hydrocarbyl group, an unsubstituted or substituted $C_{7-15}$ hydrocarbyl group, an unsubstituted or substituted $C_{4-10}$ hydrocarbyl group, an unsubstituted or substituted $C_{6-10}$ hydrocarbyl group, and an unsubstituted or substituted $C_{7-10}$ hydrocarbyl group.

In one aspect each $R_2$ group is a group selected from an unsubstituted or substituted $C_{2-19}$ hydrocarbon group, an unsubstituted or substituted $C_{3-19}$ hydrocarbon group, an unsubstituted or substituted $C_{4-19}$ hydrocarbon group, an unsubstituted or substituted $C_{5-19}$ hydrocarbon group, an unsubstituted or substituted $C_{6-19}$ hydrocarbon group, an unsubstituted or substituted $C_{7-19}$ hydrocarbon group, an unsubstituted or substituted $C_{6-15}$ hydrocarbon group, an unsubstituted or substituted $C_{7-15}$ hydrocarbon group, an unsubstituted or substituted $C_{4-10}$ to hydrocarbon group, an unsubstituted or substituted $C_{6-10}$ hydrocarbon group, and an unsubstituted or substituted $C_{7-10}$ hydrocarbon group.

In one aspect each $R_2$ group is a group selected from an unsubstituted or substituted $C_{2-19}$ alkyl group, an unsubstituted or substituted $C_{3-19}$ alkyl group, an unsubstituted or substituted $C_{4-19}$ alkyl group, an unsubstituted or substituted $C_{5-19}$ alkyl group, an unsubstituted or substituted $C_{6-19}$ alkyl group, an unsubstituted or substituted $C_{7-19}$ alkyl group, an unsubstituted or substituted $C_{6-15}$ alkyl group, an unsubstituted or substituted $C_{7-15}$ alkyl group, an unsubstituted or substituted $C_{4-10}$ alkyl group, an unsubstituted or substituted $C_{6-10}$ alkyl group, and an unsubstituted or substituted $C_{7-10}$ alkyl group.

In one aspect at least one $R_2$ group is unsubstituted. In a preferred aspect each $R_2$ group is unsubstituted.

Preferably the atom of $R_2$ bonded to the carbon of formula (I) is not substituted with an alkyl group. Preferably the atom of $R_2$ bonded to the carbon of formula (I) is unsubstituted.

In one aspect at least one $R_2$ group is substituted with one or more substituents selected from alkyl, aryl, arylalkyl and alkaryl groups. In one aspect each $R_2$ group is substituted with one or more substituents selected from alkyl, aryl, arylalkyl and alkaryl groups.

In one aspect at least one $R_2$ group is substituted with one or more alkyl groups. In one aspect each $R_2$ group is substituted with one or more alkyl groups.

In one aspect, alternate carbons in the backbone of at least one $R_2$ group, preferably each $R_2$ group, are substituted, preferably disubstituted. In this aspect, the substituents are preferably alkyl, more preferably methyl. In this aspect the substituents are preferably the same. An example of a preferred $R_2$ group in this aspect is a polyisobutene (PIB). A polyisobutene group typically has the following formula:

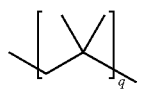
(V)

wherein q is an integer, preferably an integer from 1 to 10, more preferably from 3 to 8, such as 3, 4 or 5.

In one aspect at least one $R_2$ group is a group of formula (VI), preferably each $R_2$ group is a group of formula (VI):

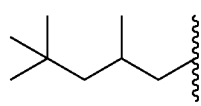
(VI)

In one aspect at least one $R_2$ group, preferably each $R_2$ group, is a group of formula (II):

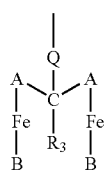
(II)

wherein Q is a bond or an unsubstituted or substituted hydrocarbyl group; and wherein $R_3$ is selected from a group consisting of hydrogen and unsubstituted or substituted $C_{1-18}$ hydrocarbyl.

In one aspect at least one $R_2$ group, preferably each $R_2$ group, is a group of formula (VII):

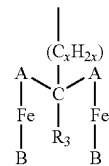
(VII)

wherein x is a positive integer; and wherein $R_3$ is selected from a group consisting of hydrogen and unsubstituted or substituted $C_{1-18}$ hydrocarbyl.

In one aspect at least one $R_2$ group, preferably each $R_2$ group, is a group of formula (III):

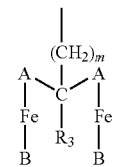
(III)

wherein m is a positive integer; and wherein $R_3$ is selected from a group consisting of hydrogen and unsubstituted or substituted $C_{1-18}$ hydrocarbyl.

Preferably m is an integer of at least 2. In one preferred aspect m is 2. In another preferred aspect m is 3. In a further preferred aspect, m is 4.

Preferably $R_3$ is selected from a group consisting of hydrogen, methyl and ethyl. In a preferred aspect $R_3$ is selected from a group consisting of hydrogen and methyl.

A and B

As discussed above the term "hydrocarbyl" as used herein relates to a group comprising at least C and H. If the hydrocarbyl group comprises more than one C then those carbons need not necessarily be linked to each other. For example, at least two of the carbons may be linked via a suitable element or group. Thus, the hydrocarbyl group may contain heteroatoms. Suitable heteroatoms will be apparent to those skilled in the art and include, for instance, sulphur, nitrogen, oxygen, silicon and phosphorus. If a heteroatom is present, it is preferably oxygen.

The unsaturated cyclic hydrocarbyl group of A and/or the unsaturated cyclic hydrocarbyl group of B may, for example be a heterocyclic group.

In one aspect each A and B contains from 3 to 10 atoms in the ring, preferably 4, 5 or 6 atoms in the ring, more preferably 5 atoms in the ring.

In one aspect each A and B is independently an unsubstituted or substituted aromatic hydrocarbyl ring. Preferably, each A and B is independently an unsubstituted or substituted aromatic carbon ring.

In one aspect, one or more of A and/or one or more of B is substituted with one or more substituents selected from alkoxy, alkyl, aryl, arylalkyl and alkaryl groups each of which substituents may be either unsubstituted or substituted. It has been found that compounds of this type typically show increased solubility compared with compounds wherein A and B are unsubstituted.

If one or more of A and/or one or more of B is substituted then they may advantageously be substituted with one or more substituents selected from alkyl, aryl, arylalkyl and alkaryl groups, preferably selected from alkyl and aryl groups, each of which substituents may be substituted or unsubstituted. If one or more of A and/or one or more of B is substituted then they are preferably substituted with one or more alkyl groups, preferably one or more $C_{1-4}$ alkyl groups.

It has been found that when one or more of A and/or one or more of B is substituted, the $R_1$—C—$R_2$ backbone may be from 1 to 20 atoms in length, such as from 1 to 10 atoms in length, preferably from 1 to 5 atoms in length, such as 3 atoms in length. Thus, in one aspect the present invention provides a composition comprising: i) at least one compound of formula (I):

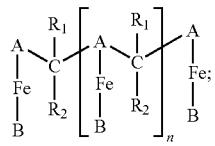
(I)

wherein $R_1$ and $R_2$ are independently selected from a group consisting of hydrogen, unsubstituted or substituted $C_{1-19}$ hydrocarbyl or a group of formula (II):

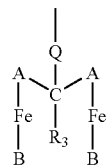
(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 1 to 20 atoms in length; wherein each A and B is independently an unsubstituted or substituted unsaturated cyclic hydrocarbyl group; wherein at least one of A and B is a substituted unsaturated cyclic hydrocarbyl group; and wherein n is an integer from 0 to 10; and ii) a diluent or carrier; wherein the compound(s) of formula (I) is present in an amount sufficient to provide, at −30° C., at least 1 wt % of iron, based on the weight of the composition.

In a preferred aspect each A and B is unsubstituted. Compounds of this type may be preferred because they may typically be less expensive than compounds wherein one or more of A and/or one or more of B is substituted.

In one aspect each A and B is the same.

In one aspect, one or more of A and/or one or more of B is cyclopentadienyl. Preferably in this aspect each A and B is cyclopentadienyl. Preferably in this aspect, each A and B is unsubstituted cyclopentadienyl.

In a preferred aspect the A and B associated with a particular Fe atom will donate electrons to said Fe atom such that the 18 electron rule is obeyed.

n

In one aspect n of formula (I) is 0, 1 or 2. Preferably n is 0.

Preferred Compositions

In one aspect, the present invention provides a composition as herein defined wherein the at least one compound of formula (I) is selected from compounds of formula (IV):

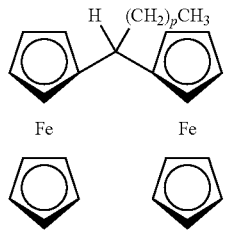
(IV)

wherein p is an integer from 4 to 18.

In one aspect p is an integer from 5 to 10, preferably p is 5. In another aspect p is an integer from 6 to 10, preferably p is 6 or 7.

Preferably, the compositions according to the present invention are free, or substantially free, of compound(s) of formula (VIII):

(VIII)

wherein A and B are as herein defined.

In one aspect the compound(s) of formula (I) is other than

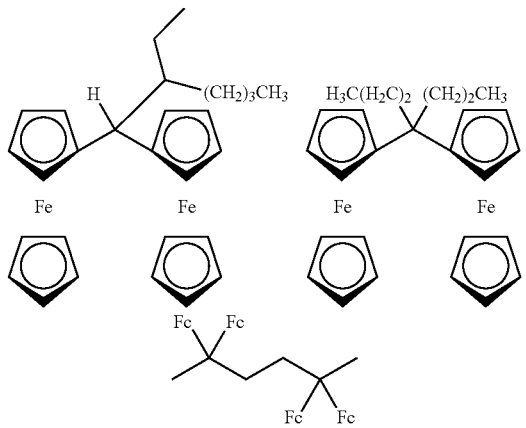

wherein Fc denotes ferrocene.

In a highly preferred embodiment the present invention provides a composition comprising: i) at least one compound of formula (IV):

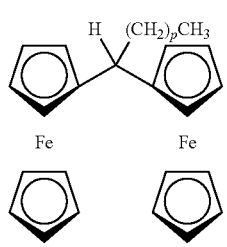
(IV)

wherein p is an integer from 6 to 10; and ii) a non-aromatic or low-aromatic diluent or carrier; wherein the compound(s) of formula (I) is present in an amount sufficient to provide, at −30° C., at least 4 wt % of iron, based on the weight of the composition.

The composition according to the present invention may comprise one or more additives for example, to improve various aspects of the fuel to which the composition is typically added or to improve various aspects of the combustion system performance. Suitable additional additives include detergents, carrier oils, anti-oxidants, corrosion inhibitors, colour stabilisers, metal deactivators, cetane number improvers, other combustion improvers, antifoams, pour point depressants, cold filter plugging depressants, wax anti-settling additives, dispersants, reodorants, dyes, smoke suppressants, lubricity agents, and other particulate filter regeneration additives.

Method for the Preparation of Compounds of Formula I

The compounds of the present invention may be made in accordance with novel or known processes. A typical general synthetic route which may be followed to prepare the compounds of the present invention is disclosed in U.S. Pat. No. 3,673,232.

Compounds of formula (I), such as those wherein n is zero and each A and B is an unsubstituted cyclopentadienyl ring, may, for example, be prepared by the condensation of two equivalents of ferrocene with one equivalent of a carbonyl compound such as a ketone or aldehyde or an equivalent such as a ketal or acetal, respectively. In U.S. Pat. No. 3,673,232 this is accomplished by addition of the carbonyl compound or equivalent to a two phase system composed of a solution of strong acid, e.g. sulphuric acid, in alcohol, e.g. methanol, and a solution of ferrocene in an organic solvent, such as toluene, or a suspension of ferrocene in ferrocene-saturated solvent, such as toluene. Compounds of formula (I), such as those wherein n is zero and one or more of A and/or B is a substituted cyclopentadienyl ring, may be prepared in an analogous manner by the condensation of two equivalents of substituted ferrocene, such as an alkyl ferrocene, with one equivalent of a carbonyl compound such as a ketone or aldehyde or an equivalent such as a ketal or acetal, respectively. Where the ferrocene or substituted ferrocene, used as starting material, is a liquid (e.g. molten) at the reaction temperature used in the preparation, then the two-phase system may comprise such liquid (e.g. molten) ferrocene compound in the absence of the organic solvent.

A mixture of starting materials may be used and a mixture of different compounds of formula (I) may thus be obtained. For example, a mixture of different aldehydes and/or a mixture of different ketones may be used as starting materials. Additionally or alternatively, a mixture of differently substituted ferrocenes or a mixture of ferrocene and one or more substituted ferrocene may be used as starting materials.

Compounds of formula (I) such as those wherein n is greater than zero, may be prepared by adjusting the molar quantity of carbonyl compound or equivalent relative to the molar quantity of ferrocene or substituted ferrocene, and/or by adjusting the addition profile of the carbonyl compound or equivalent and/or by extending reaction times. For example, reaction of 0.67 equivalents of octanal per molar equivalent of ferrocene will produce a product containing a mixture of unreacted ferrocene, a compound of formula (I) in which n is 0, a compound of formula (I) in which n is 1, and possibly one or more compounds of formula (I) wherein n is 2 or greater than 2. Addition of the octanal in two stages, first 0.6 equivalents then a further 0.3 equivalents when the reaction is substantially complete, would give a mixture containing a somewhat higher proportion of a compound of formula (I) in which n is 2, than the procedure described above involving the reaction of 0.67 equivalents of octanal. The relative proportions of oligomeric species present can also be adjusted by changing the addition profile of both the ferrocene and the carbonyl compound or equivalent. Thus a high proportion of compound of formula (I) in which n is 1 should result from treatment of the reaction product of two molar equivalents of ferrocene with one of octanal, followed by addition of a further equivalent of each of ferrocene and octanal.

Compounds of formula (I) wherein $R_1$ or $R_2$ is a group of formula (II), may be prepared by using, as the carbonyl compound or equivalent in the process outlined above, a suitable di-carbonyl species or equivalent, such as a dialdehyde or a diketone. Appropriate care needs to be taken with regard to the number of molar equivalents of each material present.

It has surprisingly been found that the compounds of formula (I) may be liquid at the temperature of interest and may therefore be used in the substantial absence of solvent.

In one aspect the present invention provides a compound of formula (I):

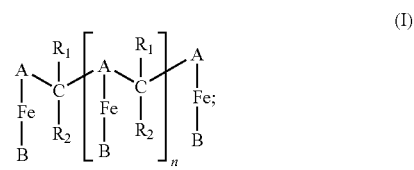

wherein $R_1$ and $R_2$ are independently selected from a group consisting of hydrogen, unsubstituted or substituted $C_{1-19}$ hydrocarbyl or a group of formula (II):

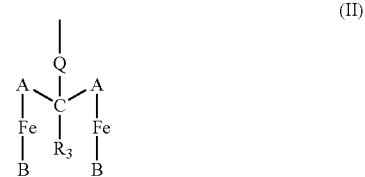

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10.

In a further aspect the present invention provides a compound of formula (I):

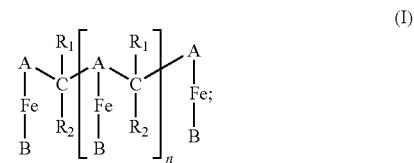

wherein $R_1$ and $R_2$ are independently selected from a group consisting of hydrogen, unsubstituted or substituted $C_{1-19}$ hydrocarbyl or a group of formula (II):

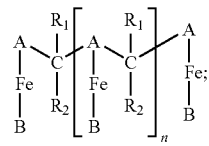

(I)

wherein $R_1$ and $R_2$ are independently selected from a group consisting of hydrogen, unsubstituted or substituted $C_{1-19}$ hydrocarbyl or a group of formula (II):

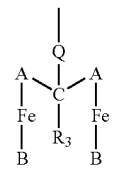

(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 5 to 20 atoms in length; wherein each A and B is independently an unsubstituted or substituted unsaturated cyclic hydrocarbyl group; and wherein n is an integer from 0 to 10; and ii) a low aromatic or non-aromatic diluent or carrier.

In this aspect, preferably the supply container is formed from HDPE. The term "HDPE" is an abbreviation for high density polyethylene.

In this aspect preferably the composition is a composition as herein defined.

Fuel

As previously mentioned, in one aspect the present invention provides a fuel composition comprising: (a) a fuel; and (b) a compound of formula (I):

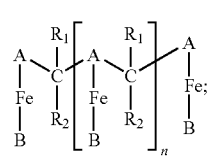

(I)

wherein $R_1$ and $R_2$ are independently selected from a group consisting of hydrogen, unsubstituted or substituted $C_{1-19}$ hydrocarbyl or a group of formula (II):

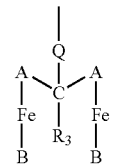

(II)

wherein Q is a bond or an unsubstituted or substituted hydrocarbyl group; wherein $R_3$ is selected from a group consisting of hydrogen and unsubstituted or substituted $C_{1-19}$ hydrocarbyl; wherein the $R_1$—C—$R_2$ backbone is from 5 to 20 atoms in length; wherein each A and B is independently an unsub-

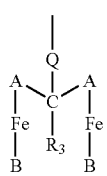

(II)

wherein Q is a bond or an unsubstituted or substituted hydrocarbyl group; wherein $R_3$ is selected from a group consisting of hydrogen and unsubstituted or substituted $C_{1-18}$ hydrocarbyl; wherein the $R_1$—C—$R_2$ backbone is from 1 to 20 atoms in length; wherein each A and B is independently an unsubstituted or substituted unsaturated cyclic hydrocarbyl group; wherein at least one of A and B is a substituted unsaturated cyclic hydrocarbyl group; and wherein n is an integer from 0 to 10; and ii) a diluent or carrier; wherein the compound(s) of formula (I) is present in an amount sufficient to provide, at −30° C., at least 1 wt % of iron, based on the weight of the composition.

Iron Content

As previously mentioned, unless otherwise stated the weight percent (wt %) of iron is measured at −30° C. and 1 atmosphere pressure.

In one aspect, the present invention provides a composition as herein defined wherein the compound(s) of formula (I) is present in an amount sufficient to provide at least 2.5 wt % of iron, preferably at least 4.0 wt % of iron, more preferably at least 5.0 wt % of iron, based on the weight of the composition.

In a preferred aspect, at −40° C. the compound(s) of formula (I) is present in an amount sufficient to provide at least 1 wt % or iron, preferably at least 2.5 wt % of iron, preferably at least 4.0 wt % of iron, more preferably at least 5.0 wt % of iron, based on the weight of the composition.

Preferably, the composition has an iron content of up to 10 wt %. A concentration of iron up to a maximum of 25.5 wt % is advantageously present in the composition according to the present invention.

It will be readily appreciated that a compound of formula (I) may exhibit even greater solubility and/or dispersibility in an aromatic diluent or carrier than in a non-aromatic or low-aromatic diluent or carrier. Thus, in one aspect, the present invention provides a composition comprising a compound of formula (I) as herein defined and an aromatic diluent or carrier. In this aspect, preferably the compound(s) of formula (I) is present at room temperature and pressure in an amount sufficient to provide at least 5 wt % of iron, based on the weight of the composition. More preferably the compound(s) of formula (I) is present at 0° C. in an amount sufficient to provide at least 5 wt % of iron, based on the weight of the composition. More preferably the compound(s) of formula (I) is present at −25° C. in an amount sufficient to provide at least 5 wt % of iron, based on the weight of the composition. In a highly preferred aspect the compound(s) of formula (I) is present at −40° C. in an amount sufficient to provide at least 5 wt % of iron, based on the weight of the composition. A suitable aromatic diluent or carrier is PLUTOsol™ APF.

Fuel Additive Dosing Apparatus

As previously mentioned, in one aspect the present invention provides a fuel additive dosing apparatus comprising a supply container formed from a plastics material incompatible with an aromatic diluent or carrier and a composition contained within the supply container comprising: i) at least one compound of formula (I):

stituted or substituted unsaturated cyclic hydrocarbyl group; and wherein n is an integer from 0 to 10.

In one aspect the fuel is a fuel for spark ignition engines such as gasoline.

Preferably the fuel is a fuel for a high compression spontaneous ignition engine.

Preferably the fuel is diesel. The diesel may be biodiesel, low sulphur diesel and ultra-low sulphur diesel.

Method

As previously mentioned, in one aspect the present invention provides a method of regenerating a particulate filter located in an exhaust system of a combustion system for fuel, which comprises contacting carbon-based particulates, present in the particulate filter, with combustion products of a composition as herein defined.

Preferably the composition is located in a container associated with the combustion system for introduction into fuel prior to combustion of the fuel in the combustion system.

Use

As previously mentioned, in one aspect the present invention provides use of a composition as herein defined for decreasing the regeneration temperature of a particulate filter located in the exhaust system of a combustion system.

When a composition according to the present invention is supplied to a fuel and the fuel is supplied to a combustion system, the composition reacts in the combustion system to produce combustion products containing iron-containing species such as iron oxide(s). Combustion of the fuel, and possibly lubricating oil or other organic carbon-based materials, within the combustion system produces combustion products which typically contain carbon-based particulates. The combustion products arising from the combustion of the composition according to the present invention which comprise solid iron-containing species such as iron oxide(s), and the carbon-based particulates, are intimately mixed in the exhaust gases from the combustion system and the particulate material is filtered out by the particulate filter. Whilst not wishing to be bound by theory, it is believed that particulate material present in the combustion products of a composition according to the present invention, which particulate material comprises iron-containing species such as iron oxide(s), is responsible for, or at least contributes to, a lowering of the ignition temperature of the carbon-based particulates and, hence, the regeneration temperature of the particulate filter. Therefore, at the operating temperature of the filter, episodes of spontaneous ignition occur and the carbon-based particulates, e.g. soot particles, are burned off to produce gaseous products.

Alternatively, means may be used to raise the temperature of the particulate filter or of the exhaust gases, thereby obtaining a so-called "forced regeneration" with the presence of the products obtained from the combustion of a composition according to the present invention, serving to reduce the input of energy required to achieve the "forced regeneration". Consequently, in combustion systems comprising particulate filters which are present in the exhaust side of the system and designed for permanent operation, and which thus need to be regenerated, the use of a composition according to the present invention may avoid the need for costly additional measures or installations, e.g. burners, electric heaters or additional catalytic systems, for burning off the carbon-based particles which have been filtered out. This means that particulate filters, e.g. diesel particulate filters, can be installed cost-effectively for permanent use without large additional expenditure. In one alternative embodiment, one or more of the above-mentioned additional measures may be employed in which case their effectiveness and/or cost effectiveness, particularly where extra fuel is burned to raise the exhaust gas temperature, may be enhanced by the use of a composition according to the present invention, or lower treat rates of a composition according to the present invention may be used.

The composition according to the present invention may be used in various types of combustion systems wherein particulate emissions are regarded as a problem, for example, spark ignition engines using gasoline, and especially gasoline direct injection engines. Preferably the composition according to the present invention is used in high compression spontaneous ignition engines, such as diesel engines.

Fuels that may be used in high compression spontaneous ignition engines are typically conventional fuels for such engines, particularly diesel fuel, including biodiesel, low sulphur diesel and ultra-low sulphur diesel.

Preferably, the composition according to the present invention is metered into the fuel, for example from a supply container. This metered addition to the fuel may, for example, take place shortly before the fuel is supplied to the combustion system which may be an internal combustion engine present in a vehicle. Alternatively, the metered addition to the fuel may, for example, take place as or shortly after the fuel is charged to the fuel tank supplying the combustion system, e.g. the fuel tank of a vehicle when the combustion system is an internal combustion engine located in the vehicle.

The composition according to the present invention is typically supplied to the fuel by means of a metering unit, e.g. by means of a metering pump, in quantities such that the iron content of the fuel is 0.1-100 ppm following the addition. On the one hand, the quantity of the composition to be added to the fuel should be great enough to ensure optimum possible burning off of the carbon-based particulates from the particulate filter but, on the other hand, should not be excessively high from the point of view of cost and the eventual partial or complete blockage of the particulate filter that may occur due to ash derived from the addition to the fuel of an excessive amount of the composition. An iron content of the fuel within the range of 1-25 ppm has proven advantageous, the optimum range being 5-15 ppm, in particular in the preferred combustion system (i.e. high compression spontaneous ignition engines).

In a preferred aspect the carbon-based particulates, present in the particulate filter, and the combustion products of the composition according to the present invention, especially solid, typically particulate, material present in the combustion products of the composition according to the present invention are intimately mixed. It is believed that the intimate mixing of the carbon-based particulates and the particulate material present in the combustion products of the composition according to the present invention results in:

(a) at least a portion of the surface of the carbon-based particulates being coated with solid combustion products of the composition according to the present invention;

(b) at least a portion of the surface of solid combustion products of the composition according to the present invention being coated with the carbon-based particulates; and/or (c) solid combustion products of the composition according to the present invention being intimately mixed with particles of the carbon-based particulates.

In a preferred aspect the carbon-based particulates and the combustion products of the composition according to the present invention, present in the particulate filter are exposed to both heat and an oxidant gas (e.g. $O_2$ or $NO_2$), preferably both the heat and oxidant gas are supplied within the exhaust gases from the combustion system.

Aspects of the invention are defined in the appended claims.

The present invention will now be described in further detail in the following examples.

EXAMPLES

Example 1

Solubility in Aromatic Solvent

The existence of any effects on solubility and solution viscosity due to changes in the substitution on the aromatic ring and/or on the bridging group was examined by preparation of a series of bridged ferrocenes i.e. compounds according to formula (I) of the present invention. Two sets of standard conditions were employed for the preparation and isolation of these products, for use with un-substituted and alkylated ferrocene, respectively. Variation of these conditions to arrive at optimum syntheses of particular derivatives, in particular to maximise the yield on ferrocene, minimise formation of side-products such as alkenylated ferrocenes and minimise the effort required to separate the desired soluble products, is deemed to be within the scope of those skilled in the art.

Preparation of Bridged Ferrocenes

Sulphuric acid (98 wt % $H_2SO_4$, 196 g, 2.0 mol) was added carefully to methanol (214.4 g, 6.7 mol) in a conical flask. The solution temperature was maintained at below 40° C. by cooling (ice-water bath) and changing the addition rate. The solution was transferred to a jacketed, well-baffled one litre reactor equipped with an overhead turbine agitator, reflux condenser, dropping funnel, thermometer and bottom outlet. The reactor was then further charged with powdered ferrocene (130.2 g, 0.7 mol) washed in with toluene (130 g).

The reactor contents were then warmed to 80±2° C. by the circulation of hot oil through the jacket, and were rapidly stirred to create an emulsion of the methanolic phase and toluene slurry. The carbonyl compound (0.35 mol, 1 equivalent) was then charged to the dropping funnel and added dropwise to the reactor over about 15 minutes at a substantially uniform rate. The reactor contents were then held, with strong agitation, at 80°±2° C. for 6 hours before being allowed to cool to ambient temperature overnight.

Where ferrocene crystallised out on cooling this was removed by filtration. Further toluene (130 g) was then added to the liquid phases, and after a further 15 minutes stirring, water (10 cm$^3$) was added, where required to aid phase separation and agitation stopped. The methanol/sulphuric acid phase was then separated and the organic phase washed with aqueous base (2×200 cm$^3$ 10% $NaHCO_3$ or NaOH) then water (2×200 cm$^3$), dried over anhydrous sodium sulphate and separated by filtration to remove the drying agent. Crude product mixture, contaminated by varying amounts of unreacted ferrocene was recovered by removal of the toluene at the rotary evaporator.

Isolation of Bridged Ferrocenes

Solid materials were ground in a pestle and mortar in the presence of heptane and filtered to recover solids. The process was repeated until thin layer chromatography (Merck Aluminium oxide 150 $F_{254}$ (Type T) stationary phase, 3 to 4 parts EtOH to 1$H_2O$ as mobile phase) indicated the solids to be substantially free of ferrocene. The material was then dissolved in a minimal quantity of hot heptane, hot-filtered, then recovered by recrystallisation on cooling.

Crude products were on occasion oils free or substantially free of solids. The products were found to phase-separate from heptane on refrigeration and so were separated from ferrocene, which tended to remain in solution. Again, progress was monitored by tlc.

On occasion crude products comprised mixtures of oil and solid. Here, a judgement was made as to which if the above techniques was more likely to be appropriate (i.e. a sticky solid would be ground with heptane in a pestle and mortar, an oil containing suspended solids would be dissolved in the minimum of hot heptane, then refrigerated). Where time and quantity of material available permitted, trial separations were performed. Again, purification method selection and/or progress was monitored by tlc.

Final and near-complete removal of ferrocene from solid, oil or mixed phases was achieved by sublimation at <0.6 mBar, 80° C.

Preparation of Bridged, Alkylated Ferrocenes

Alkylated ferrocenes provided reaction products with carbonyl compounds that were viscous oils at ambient temperature, becoming highly mobile on warming. Accordingly, emulsions comprising methanolic sulphuric acid and solutions of alkylated ferrocenes in toluene were treated with 0.5 equivalents of carbonyl compound at 80° C., as above. The organic phases were separated, washed with base and dried. Toluene solvent and unreacted alkylated ferrocenes were removed by distillation to leave the products as oils. No further isolation was required.

Determination of Product Properties

Iron contents of the samples were estimated on the basis of C/H/N analysis (Leco CHNS 932). This assumes that all isolated products were free, or substantially so, of unreacted carbonyl compounds, or oxygen-containing reaction products thereof, Ferrocene contents of the samples were determined by GC/MS on a Finnigan MAT GCQ (GC/MS), using a Supelco MDN-5S fused silica capillary column (30 m×0.25 mm i.d. 0.25μ film thickness) initial temperature 40° C., held for 2.1 minutes before ramping to 200° C. at 10° C.min$^{-1}$ before holding for 20 minutes, injector temperature 275° C., He flow 40 cm·s$^{-1}$ constant velocity, calibrated against pure ferrocene.

Where suitably crystalline materials could be obtained, further characterisation was performed using $^1H$ and $^{13}C$ nmr (Bruker AC200). Integration of cyclopentadienyl protons [shift range 4-4.5 ppm downfield of TMS (tetramethylsilane) in $C_6D_6$] against those of any carbonyl-derived bridging unit was used, where possible, to provide qualitative information on the degree of oligomer formation. All spectra were run in $C_6D_6$ solution with shifts reported relative to TMS. Where possible, carbon atoms were identified as methyl, methylene or methyne, via the DEPT (Distortionless Enhancement by Polarisation Transfer) experiment.

Solubility testing was undertaken using the estimate of Fe content from C/H/N analysis. Since the iron content of ferrocene is known to be 30 wt %, that present as condensation products was estimated by difference. This procedure assumes the products below to contain substantially only C, H and Fe. Masses of product(s) sufficient to provide the required concentration of iron as condensation products were weighed into screw-cap vials and made up to 10.00 g with toluene. The samples were capped, shaken or swirled until homogenous then sealed using Parafilm™. The vials were then kept in an ethylene glycol/water filled bath held at −30° C. and periodically inspected for the appearance of solids or separation of liquid phases. After at least one week solids were separated by rapid filtration and soluble products isolated by removal of solvent under vacuum.

Following analysis of the solids, maximum and minimum solubilities were estimated from the mass balance Viscosities of 2.5 wt % iron solutions were determined using a Bohlin Instruments CVO rheometer using a 4° 40 mm cone and plate at shear rates of either 2 Pa or 0.5 Pa. .

TABLE 1

Theoretical Analyses for Condensation Products of Ferrocenes with Carbonyl Compounds

| Compound No. | Carbonyl Compound | Calculated for n = 0 | | | Calculated for n = 1 | | |
|---|---|---|---|---|---|---|---|
| | | C (% m/m) | H (% m/m) | Fe (% m/m) | C (% m/m) | H (% m/m) | Fe (% m/m) |
| 1. | 2-Ethylhexanal | 69.72 | 7.12 | 23.16 | 70.96 | 7.52 | 21.52 |
| 2. | Acetonyl acetone | 67.18 | 5.65 | 27.17 | 67.52 | 5.68 | 26.80 |
| 3. | Heptan-4-one | 71.00 | 7.70 | 21.30 | 71.94 | 7.99 | 20.07 |
| 4. | Pentanal | 68.20 | 6.42 | 25.37 | 69.18 | 6.69 | 24.13 |
| 5. | 2,4-Pentanedione | 66.86 | 5.50 | 27.64 | 67.16 | 5.51 | 27.33 |
| 6. | Pentan-3-one | 70.17 | 7.33 | 22.50 | 70.96 | 7.52 | 21.52 |

The terms calculated for n=0 and n=1 in the table above refer, respectively, to compounds of formula (I) wherein n is 0 or 1. From the $^1$H nmr spectra integration of the methyl group protons against cyclopentadienyl ones suggested that, assuming only species wherein n=0 and n=1 to be present, about 9 mol % n=1 had resulted.

Compounds 1, 2, 4 and 5 were prepared using ferrocene. Compounds 3 and 6 were made using ethylferrocene such that one of A or B in formula (I) is ethylcyclopentadienyl, the other being, in each case, cyclopentadienyl.

TABLE 2

Analytical Details for Isolated Compositions.

| Compound No. | Carbonyl Compound | Found | | | Implied [Fe] (% m/m) | Ferrocene Content (% m/m) | Iron as product (% m/m) |
|---|---|---|---|---|---|---|---|
| | | C (% m/m) | H (% m/m) | | | | |
| 1 | 2-Ethylhexanal | 73.20 | 8.15 | | 18.65 | <1.0 | 18.65 |
| 2 | Acetonyl acetone | 76.40 | 7.04 | | 16.56 | 3.50 | 15.51 |
| 3 | Heptan-4-one | 68.85 | 6.90 | | 24.25 | <1.0 | 24.25 |
| 4 | Pentanal | 68.79 | 6.94 | | 24.27 | 2.0 | 23.67 |
| 5 | 2,4-Pentanedione | 67.03 | 5.88 | | 27.09 | <1.0 | 27.09 |
| 6 | Pentan-3-one | 70.50 | 7.45 | | 22.05 | <1.0 | 22.05 |

TABLE 3

Outcomes of Solubility Determination for the Isolated Compositions

| Compound No. | Carbonyl Compound | Solubility in Toluene at −30° C. | | Solubility of Fe as product |
|---|---|---|---|---|
| | | 2.5 wt % Fe | 5.0 wt % Fe | |
| 1 | 2-Ethylhexanal | Clear | Clear | |
| 2 | Acetonyl acetone | Powder | Powder | Solid not characterisable |
| 3 | Heptan-4-one | Clear | Solids | Insufficient solids to characterise |
| 4 | Pentanal | Clear | Clear | |
| 5 | 2,4-Pentanedione | Solids | Solids | 2.05 to 2.26 wt % by mass balance |
| 6 | Pentan-3-one | Deposit | Deposit | Minimal deposition in both cases |

TABLE 3a

NMR Spectroscopy Details for Derivatives Isolated as Crystalline Materials

| 5 | 2,4-Pentanedione | 1.308 (s, 6H) | 30.77 ($CH_3$), 33.47 ($CH_2$) and 101.51 ($CH_3$—C—$CH_2$) |
|---|---|---|---|
| | Cyclopentadienyl | 3.93 to 4.01 (m, 18H) | 66.27, 66.73 and 68.89 |

For comparison, the solubility of iron as ferrocene in toluene was around 1 wt % Dilutions of samples of 5 wt % Fe as the product of compound 1 established the solubility limit in toluene of this preferred material to be slightly less than 3.2 wt % at −30° C.

TABLE 4

GC/MS Data

| Compound No. | Carbonyl source | Component/(level) | Comments |
|---|---|---|---|
| 1 | 2-Ethylhexanal | 2-ethylhexenyl ferrocene (major) | Many isomers, parent ion 296, loss of various alkene fragments |
|  |  | Bis 2-ethylhexenyl ferrocene (minor) | Isomers, parent ion at 406, typically loss of heptene observed |
|  |  | 1,1-diferrocenyl 2-ethylhexane (trace) | Parent at 482, first loss heptene |
| 4 | Pentanal | 1,1-diferrocenylpentane (good purity) | Parent at 440, first loss $C_4H_9$ |

TABLE 5

Viscosity Data of Compositions in Toluene Solution at 2.5 wt % Fe

| Compound | Carbonyl Source | Metallocene | Viscosity at −30° C. (mPas) |
|---|---|---|---|
| 1 | 2-Ethylhexanal | Ferrocene | 5.1 to 6.4 |
| 3 | Heptan-4-one | Ethylferrocene | 5.1 |
| 4 | Pentanal | Ferrocene | 5.4 |
| 5 | 2,4-Pentanedione | Ferrocene | 4.7 |
| 6 | Pentan-3-one | Ethylferrocene | 5.3 |

Interpretation of Data

Compound 1 demonstrates that branched aldehydes may also be used to prepare 1,1-diferrocenyl alkanes. The GC/MS data for compound 1 also show that where an aldehyde, and by inference a ketone, is branched at the position a to the carbonyl then a propensity to form alkenyl-substituted ferrocene exists. Without wishing to be bound by theory it is suspected that an intermediate hydroxyalkyl ferrocene forms which may react with a further molecule of ferrocene to yield a diferrocenylalkyl or may dehydrate to yield the alkene. Experimental conditions may be changed by routine experimentation to minimise formation of such products.

Example 2

Solubility in Non-Aromatic or Low-Aromatic Solvent

A one litre three-necked flask fitted with an overhead stirrer driving a turbine impeller, and as and when appropriate, a thermometer, reflux condenser and dropping funnel was charged with methanol (158.4 g, 4.95 mol). Sulphuric acid (98%, 147 g, 1.47 mol) was then added, with stirring and cooling to keep the temperature below 40° C. The solution was rapidly stirred (500 rev/min) and ferrocene (139.5 g, 0.75 mol) and toluene (139.5 g) charged. The entire mixture was then heated to reflux temperature. At this temperature the aldehyde, ketone or equivalent (0.45 mol) was then added at a steady rate, via the dropping funnel, over about one hour. Once the addition was complete, the reaction mixture was stirred at the lowest temperature of either a rapid reflux or 95° C. during a further five hours before cooling to about 30° C.

After cooling, further toluene (139.5 g) was added and the emulsion stirred for a further ten minutes. The two phases were then separated using a separating funnel. The upper, toluene, layer was then removed and neutralised in a reservoir using saturated sodium hydrogen carbonate (150 cm3). After neutralisation the phases were left to stand for a minimum of two hours, preferably overnight, to separate. The aqueous phase was then discarded and the toluene phase filtered prior to removal of toluene and excess aldehyde, ketone or equivalent by distillation under the vacuum provided by a water jet pump.

TABLE 6

Carbonyl Compounds Used

| Carbonyl or equivalent | Molecular formula | Boiling point ° C. |
|---|---|---|
| Pentan-2-one | $C_5H_{10}O$ | 101-103 |
| Perrtan-3-one | $C_5H_{10}O$ | 101-103 |
| Hexanal | $C_6H_{12}O$ | 131 |
| Hexan-3-one | $C_6H_{12}O$ | 125 |
| Heptanal | $C_7H_{14}O$ | 153 |
| Heptan-2-one | $C_7H_{14}O$ | 150-152 |
| Octanal | $C_8H_{16}O$ | 163 |
| Octan-2-one | $C_8H_{16}O$ | 173 |
| Nonanal | $C_9H_{18}O$ | 93 (31 hPa) |
| Decanal | $C_{10}H_{20}O$ | 209 |
| ethyl-3-oxobutyrate | $C_6H_{10}O_3$ | 180 |

The solubilities of the products of the above reactions were determined on a weight percent iron basis. Solids isolated as described above were assumed to comprise essentially pure samples of the desired material. Solutions at 5 wt % iron in Isopar L were prepared on this basis, sealed into vials and stored at −30° C. during at least one week. The solutions were then removed, rapidly filtered, and the iron content of the liquid phase determined by X-ray spectroscopy using ferrocene as a standard. The solubility of iron as ferrocene itself in Isopar L at −30° C. was determined to be 0.22 wt % by this technique.

TABLE 7

Iron content of Isopar L solutions at −30° C.

| Desired product | Carbonyl Compound | Iron content (wt %) |
|---|---|---|
| 2,2-bis-(ferrocenyl)-pentane | Pentan-2-one | 2.62 |
| 3,3-bis-(ferrocenyl)-pentane | Pentan-3-one | 1.71 |
| 1,1-bis-(ferrocenyl)-hexane | Hexanal | 3.99 |
| 1,1-bis-(ferrocenyl)-hexane | Hexanal | 4.89* |
| 3,3-bis-(ferrocenyl)-hexane | Hexan-3-one | 1.38 |
| 1,1-bis-(ferrocenyl)-heptane | Heptanal | 4.05 |
| 2,2-bis-(ferrocenyl)-heptane | Heptan-2-one | 3.29 |
| 1,1-bis-(ferrocenyl)-octane | Octanal | 4.60 |
| 1,1-bis-(ferrocenyl)-octane | Octanal | 4.88* |
| 2,2-bis-(ferrocenyl)-octane | Octan-2-one | 2.72 |
| 1,1-bis-(ferrocenyl)-nonane | Nonanal | 4.96 |
| 1,1-bis-(ferrocenyl)-decane | Decanal | 4.41 |

TABLE 7-continued

Iron content of Isopar L solutions at −30° C.

| Desired product | Carbonyl Compound | Iron content (wt %) |
|---|---|---|
| 3,3-bis-(ferrocenyl)-butyl acetate | 3-oxo-butyl acetate | 2.30 |
| Ferrocene | Not applicable | 0.22 |

*= sample first purified by dissolving in minimum heptane, cooling to recrystallise ferrocene, filtration and removal of solvent under vacuum.

Preparation of Condensation Products of Alkylated Ferrocenes

The procedure described in detail above was followed, save that it was performed on an 8-fold larger scale and in the absence of toluene solvent, using ethyl- and butyl-ferrocenes as starting materials. The term 'mass balance' refers to the percentage ratio of the found weight of product on removal of volatiles at the rotary evaporator to the anticipated yield, assuming complete conversion to the target species. Molecular weight was determined by cryoscopy in benzene and indicates, once the level of unreacted starting material is taken into account, the degree to which oligomers (n=1 or higher in formula (I)) are present.

TABLE 8

Reactions from Ethylferrocene

| Carbonyl compound | Temp (° C.) | Mass balance (%) | Unreacted ethyl-ferrocene (%) | Theory/found MWt (Dalton) |
|---|---|---|---|---|
| Acetone | 80 | 72.2 | 11.7 | 468/468 |
| Acetone | 98 | 76.4 | 14.4 | 468/523 |
| Propanal | | 81.8 | 7.5 | 468/500 |
| Pentanal | 90 | 86.6 | 0.5 | 496/494 |
| Pentan-2-one | 95 | 41.3 | 33.2 | 496/449 |
| Pentan-3-one | 80 | 24.2 | 15.0 | 496/418 |
| Heptanal | 98 | 88.6 | 3.2 | 524/525 |
| Heptan-4-one | 97 | 16.0 | 19.0 | 524/532 |

TABLE 9

Reactions from Butylferrocene

| Carbonyl compound | Temp (° C.) | Mass balance (%) | Unreacted butyl-ferrocene (%) | Theory/found MWt (Dalton) |
|---|---|---|---|---|
| Acetone | 80 | 60.1 | 8.8 | 524/503 |
| Acetone* | 91 | 50.4 | 8.4 | 524/472 |
| Acetone | 90 | 70.9 | 11.9 | 524/502 |
| Propanal | 97 | 65.3 | 4.3 | 524/536 |
| Pentanal | 90 | 75.6 | 5.0 | 552/594 |
| Heptanal | 95 | 73.3 | 1.9 | 580/594 |

*2 hour reaction time only

Example 3

HDPE Container Compatibility Testing

Tests were carried out on an additive container fabricated from HDPE which contained an aromatic solvent. Aromatic solvent loss by permeation through the walls of the container at a temperature of 60° C. was recorded. These results were used to calculate the projected annual permeation loss which is displayed in Table 10 below.

TABLE 10

| Container Type | Solvent | Projected Annual Permeation Loss |
|---|---|---|
| Uncoated HDPE | Plutosol F aromatic solvent | 43.9% |

Further tests were carried out on three different combinations of container and solvent. Results of loss permeation tests at 40° C. were used to calculate the projected annual permeation loss. The projected annual permeation loss for each combination is displayed in Table 11 below.

TABLE 11

| | Container Type | Solvent | Projected Annual Permeation Loss |
|---|---|---|---|
| A | Uncoated HDPE | Isopar L aliphatic solvent | 0.61% |
| B | Co-extruded HDPE with a polyamide barrier | Plutosol F aromatic solvent | 0.12% |
| C | Barrier coated HDPE (fluorinated to level 5) | Plutosol F aromatic solvent | 0.047% |

The results in Table 10 show that the permeation loss which occurs for an aromatic solvent in an uncoated HDPE container is extremely high. These results clearly demonstrate that aromatic solvents are incompatible with uncoated HDPE containers.

The results in Table 11 show that permeation loss figures for each combination of solvent and container are comparable (all less than 1%). Thus use of an aliphatic solvent in an uncoated HDPE container (A) is a viable alternative to prior art use of an aromatic solvent in a modified HDPE container (B or C).

Example 4

Solubility in Non-Aromatic or Low-Aromatic Solvent

Preparation of Compounds

Sulphuric acid (98% % $H_2SO_4$, 196 g, 2.0 mol) was added carefully to methanol (214.4 g, 6.7 mol) in a round bottom 3 necked flask cooled to below 10° C. in an ice/acetone bath.

The solution was transferred to a one litre reactor equipped with an overhead stirrer, reflux condenser, dropping funnel, and thermometer. The reactor was then further charged with powdered ferrocene (186 g, 1 mol) washed in with toluene (186 g).

The reactor contents were then warmed, with vigorous stirring, to 85° C. The aldehyde (0.5 mol) was added dropwise to the reactor over about 1 hour and the reactor contents were held, with strong agitation, at 85° C. for 5 hours before being allowed to cool to ambient temperature and left to stand overnight.

The methanol/sulphuric acid phase was then separated and the organic phase washed with aqueous base (2×200 cm³ 10% $NaHCO_3$) then water (2×200 cm³), dried over anhydrous sodium sulphate and filtered. The crude product was recovered by removal of the toluene at the rotary evaporator.

The un-reacted ferrocene was removed by vacuum sublimation (24 hrs. 70° C.<1 mmHg). Ferrocene contents of the samples were determined by GC/MS on a Finnigan MAT GCQ, using a Supelco MDN-5S fused silica capillary column (30 m×0.25 mm i.d. 0.25µ film thickness). The initial temperature 40° C. was held for 2.1 minutes before ramping to 200° C. at 10° C.min$^{-1}$ before holding for 20 minutes. Injector temperature was 275° C. and He flow 40 cm·s$^{-1}$ constant velocity. Calibration was against pure ferrocene. This procedure also provided a qualitative guide to the purity of the product and for mass spectra of the components.

TABLE 12

| Compound | Aldehyde | | C % m/m | H % m/m | Ferrocene % m/m | Comments on GC/MS data |
|---|---|---|---|---|---|---|
| 7. | 3,5,5-Trimethylhexanal | Ferrocene | 71.14 | 7.82 | 0.3 | Mw pk 496, no higher oligomers. |
| 8. | Valeraldehyde | Ferrocene | 68.96 | 6.69 | <0.3 | Mw pk 440. Small impurity of higher oligomer mw 508 |

The result from compound 7 shows that where an aldehyde is branched at the β-position the alkylene-bridged diferrocene species predominates.

In addition to the samples prepared as set out above, additional materials were prepared by the method of U.S. Pat. No. 3,673,232. These compounds are shown in table 13.

TABLE 13

| Compound | Substituted Ferrocene | Carbonyl compound | Product |
|---|---|---|---|
| 9. | Ethylferrocene | Pentanal | 1,1-bis(ethylferrocenyl)pentane |
| 10. | Butylferrocene | Pentanal | 1,1-bis(butylferrocenyl)pentane |

Solubility Testing

The solubility of the isolated samples was determined in Isopar L solvent. For the isolated samples of compounds 7 and 8 the C/H/N analysis was used to indicate the iron content. For compounds 9 and 10 the theoretical iron content was assumed. Solutions were then prepared, at ambient temperatures or with slight warming as required, to a nominal iron content 5 wt % The samples were then sealed and immersed in a bath of ethylene glycol/water cooled and thermostatted to −30° C. during 120 hours.

The samples were then individually removed from the bath, taken up into a 10 cm$^3$ syringe then discharged to a second vial with filtration via a Whatman Anotop 25 0.02 μm in-line filter with Luer hub. Iron contents were then determined by X-ray fluorescence spectroscopy in an Oxford Instruments ED2000 Ag analyser. The analyser was calibrated against standards of ferrocene in toluene at iron concentrations of 0.5 through 3.0 wt % by 0.5 wt % intervals and against ferrocene in Isopar L 0.5 and 1.0 wt % (approximate ambient temperature solubility limit). Where required, dilution of sample materials was employed to bring the concentration within the range of the calibration.

The results obtained are shown in table 14.

TABLE 14

| Compound | Wt of sample (g) | Wt of sample and solvent (g) | Appearance/ease of filtration | Solubility (% m/m Fe) |
|---|---|---|---|---|
| 7 | 2.42 | 10.02 | Thick slurry of tan powder | 4.1 |
| 8 | 2.12 | 10.12 | Significant quantity of tan powder, but filters well | 3.1 |
| 9 | 2.29 | 10.09 | Clear, filters well | 5.0 |
| 10 | 2.60 | 10.55 | Clear, but hard to filter | 4.8 |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims

The invention claimed is:

1. A composition comprising:
   i) at least one compound of formula (I):

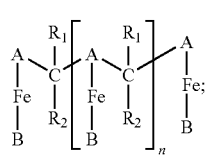

wherein each $R_1$ is hydrogen and each $R_2$ is independently selected from a group consisting of hydrogen, unsubstituted or substituted $C_{1-19}$ hydrocarbyl or a group of formula (II):

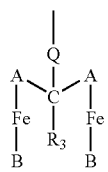

wherein Q is a bond or an unsubstituted or substituted hydrocarbyl group;
   wherein $R_3$ is selected from a group consisting of hydrogen and unsubstituted or substituted $C_{1-18}$ hydrocarbyl;
   wherein the $R_1$—C—$R_2$ backbone is from 5 to 20 atoms in length;
   wherein each A and B is independently an unsubstituted or substituted unsaturated cyclic hydrocarbyl group; and
   wherein n is an integer from 0 to 10; and
   ii) a diluent or carrier;
   wherein the compound(s) of formula (I) is present in an amount sufficient to provide, at −30° C., at least 1 wt % of iron, based on the weight of the composition, and wherein the diluent or carrier is a low-aromatic or non-aromatic diluent or carrier.

2. A composition according to claim 1 wherein the diluent or carrier is a solvent.

3. A composition according to claim 1, wherein when the $R_1$—C—$R_2$ backbone is 5, 7 or 19 atoms in length, the backbone is substituted.

4. A composition according to claim 1 wherein at least one or each R2 group is independently selected from H and unsubstituted or substituted $C_{1-19}$ alkyl group.

5. A composition according to claim 1 wherein at least one or each $R_2$ group is an unsubstituted or substituted $C_{4-19}$ alkyl group.

6. A composition according to claim 1 wherein at least one or each $R_2$ group is an unsubstituted or substituted $C_{4-10}$ alkyl group.

7. A composition according to claim 1 wherein at least one or each $R_2$ group is an unsubstituted or substituted $C_{7-19}$ alkyl group.

8. A composition according to claim 7 wherein at least one or each $R_2$ group is an unsubstituted or substituted $C_{7-15}$ alkyl group.

9. A composition according to claim 8 wherein at least one or each $R_2$ group is an unsubstituted or substituted $C_{7-10}$ alkyl group.

10. A composition according to claim 1 wherein at least one or each $R_2$ group is unsubstituted.

11. A composition according to claim 1 wherein at least one or each $R_2$ group is substituted with one or more substituents selected from alkyl, aryl, arylalkyl and alkaryl groups.

12. A composition according to claim 11 wherein at least one or each $R_2$ group is substituted with one or more alkyl groups.

13. A composition according to claim 1 wherein at least one or each $R_2$ group is a group of formula (II):

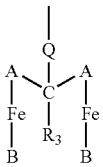

wherein Q is a bond or an unsubstituted or substituted hydrocarbyl group.

14. A composition according to claim 13 wherein at least one or each $R_2$ group is a group of formula (III):

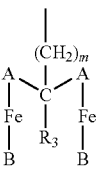

wherein m is a positive integer.

15. A composition according to claim 14 wherein m is an integer of at least 2.

16. A composition according to claim 14, wherein $R_3$ is selected from a group consisting of hydrogen, methyl and ethyl.

17. A composition according to claim 1 wherein each A and B contains from 3 to 10 atoms in the ring.

18. A composition according to claim 1, wherein each A and B contains 4, 5 or 6 atoms in the ring.

19. A composition according to claim 1, wherein each A and B group contains 5 atoms in the ring.

20. A composition according to claim 1, wherein each A and B is independently an unsubstituted or substituted aromatic hydrocarbyl ring.

21. A composition according to claim 1, wherein each A and B is independently an unsubstituted or substituted aromatic carbon ring.

22. A composition according to claim 1, wherein one or more of A and/or one or more of B is substituted with one or more substituents selected from alkyl, aryl, arylalkyl and alkaryl groups.

23. A composition according to claim 1, wherein one or more of A and/or one or more of B is substituted with one or more alkyl groups.

24. A composition according to claim 1, wherein each A and B is unsubstituted.

25. A composition according to claim 1, wherein each A and B is the same.

26. A composition according to claim 1, wherein each A and B is cyclopentadienyl.

27. A composition according to claim 1 wherein n is 0, 1 or 2.

28. A composition according to claim 1 wherein n is 0.

29. A composition according to claim 1 wherein the one or more compounds of formula (I) are selected from compounds of formula (IV):

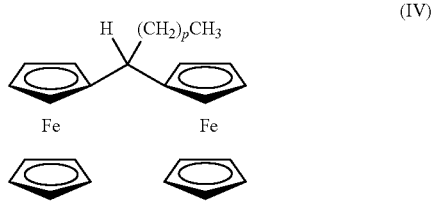

(IV)

wherein p is an integer from 4 to 18.

30. A composition according to claim 29 wherein p is an integer from 5 to 10.

31. A composition according to claim 29 wherein p is 5.

32. A composition according to claim 29 wherein p is 6 or 7.

33. A composition according to claim 1 wherein the one or more compound of formula (I) is present in an amount sufficient to provide, at −30° C., at least 2.5 wt % of iron, based on the weight of the composition.

34. A composition according to claim 1 wherein the one or more compound of formula (I) is present in an amount sufficient to provide, at −30° C., at least 4.0 wt % of iron, based on the weight of the composition.

35. A composition according to claim 1 wherein the one or more compound of formula (I) is present in an amount sufficient to provide, at −30° C., at least 5.0 wt % of iron, based on the weight of the composition.

36. A composition according to claim 1, wherein the one or more compound of formula (I) is present in an amount sufficient to provide, at −40° C., at least 1 wt % of iron, based on the weight of the composition.

37. A fuel additive dosing apparatus comprising:
(a) a supply container formed from a plastics material incompatible with an aromatic diluent or carrier; and
(b) a composition contained within the supply container comprising:
i) at least one compound of formula (I):

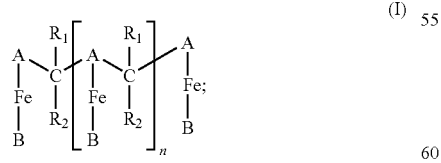

(I)

wherein each $R_1$ is hydrogen and each $R_2$ is independently selected from a group consisting of hydrogen, unsubstituted or substituted $C_{1-19}$ hydrocarbyl or a group of formula (II):

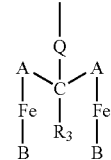

(II)

wherein Q is a bond or an unsubstituted or substituted hydrocarbyl group;
wherein $R_3$ is selected from a group consisting of hydrogen and unsubstituted or substituted $C_{1-18}$ hydrocarbyl;
wherein the $R_1$—C—$R_2$ backbone is from 5 to 20 atoms in length;
wherein each A and B is independently an unsubstituted or substituted unsaturated cyclic hydrocarbyl group; and
wherein n is an integer from 0 to 10; and
ii) a low aromatic or non-aromatic diluent or carrier having a total aromatic substance content of less than 5 wt %, wherein the compound(s) of formula (I) is present in an amount sufficient to provide, at −30° C., at least 1 wt % of iron, based on the weight of the composition.

38. A fuel dosing apparatus according to claim 37 wherein the supply container is formed from HDPE.

39. A fuel composition comprising:
(a) a fuel;
(b) a compound of formula (I):

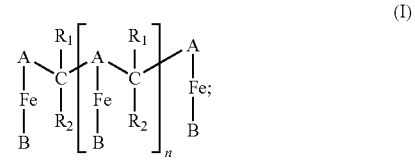

(I)

wherein each $R_1$ is hydrogen and each $R_2$ is independently selected from a group consisting of hydrogen, unsubstituted or substituted $C_{1-19}$ hydrocarbyl or a group of formula (II):

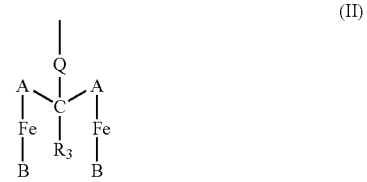

(II)

wherein Q is a bond or an unsubstituted or substituted hydrocarbyl group;
wherein $R_3$ is selected from a group consisting of hydrogen and unsubstituted or substituted $C_{1-18}$ hydrocarbyl;
wherein the $R_1$—C—$R_2$ backbone is from 5 to 20 atoms in length;
wherein each A and B is independently an unsubstituted or substituted unsaturated cyclic hydrocarbyl group; and
wherein n is an integer from 0 to 10; and
c) a low-aromatic or non-aromatic diluent or carrier;
wherein the compound(s) of formula (I) is present in an amount sufficient to provide, at −30° C., at least 1 wt % of iron, based on the weight of the composition.

* * * * *